United States Patent
Clark et al.

(10) Patent No.: US 7,361,798 B2
(45) Date of Patent: Apr. 22, 2008

(54) PRODUCTION OF DIALKYLBENZENES

(75) Inventors: Michael C. Clark, Pasadena, TX (US); Ronald J. Cimini, Friendswood, TX (US); Jane C. Cheng, Bridgewater, NJ (US); David L. Stern, Baton Rouge, LA (US); John Scott Buchanan, Lambertville, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 696 days.

(21) Appl. No.: 10/946,553

(22) Filed: Sep. 21, 2004

(65) Prior Publication Data

US 2005/0075523 A1 Apr. 7, 2005

Related U.S. Application Data

(60) Provisional application No. 60/508,831, filed on Oct. 3, 2003.

(51) Int. Cl.
*C07C 5/22* (2006.01)
*C07C 1/20* (2006.01)
(52) U.S. Cl. ..................... 585/475; 585/323
(58) Field of Classification Search ............... 585/475, 585/323
See application file for complete search history.

(56) References Cited

U.S. PATENT DOCUMENTS

| | | | |
|---|---|---|---|
| 2,848,514 A | 8/1958 | De Keizer et al. | 260/671 |
| 3,763,259 A | 10/1973 | Hervert | 260/671 P |
| 4,347,393 A | 8/1982 | Miki | 585/323 |
| 4,375,575 A | 3/1983 | Slaugh | 585/480 |
| 4,822,943 A | 4/1989 | Burress | 585/467 |
| 5,329,059 A | 7/1994 | Marler | 585/475 |
| 5,929,296 A | 7/1999 | Merlen et al. | 585/475 |
| 6,037,512 A | 3/2000 | Benazzi et al. | 585/446 |
| 6,049,018 A | 4/2000 | Calabro et al. | 585/446 |
| 6,512,154 B1 | 1/2003 | Magne-Drisch et al. | 585/470 |
| 2003/0125591 A1 | 7/2003 | Weber et al. | 585/323 |

FOREIGN PATENT DOCUMENTS

| | | |
|---|---|---|
| EP | 1 106 592 A | 6/2001 |
| GB | 755956 | 11/1956 |
| GB | 786305 | 11/1957 |

OTHER PUBLICATIONS

Abstract, NL 85,204, entitled "Transalkylation of Alkylated Benzenes", dated May 15, 1957.

*Primary Examiner*—Thuan Dinh Dang
(74) *Attorney, Agent, or Firm*—Darryl Tyus; Xiaobing Feng

(57) ABSTRACT

The invention relates to a process for producing a desired dialkylbenzene isomer having a formula $R_2C_6H_4$, where R is an alkyl substituent, by contacting a polyalkylbenzene compound of formula $R_nC_6H_{6-n}$, where n is an integer between 2 and 4, with a monoalkylbenzene compound of formula $RC_6H_5$ in the presence of a molecular sieve catalyst under reaction conditions sufficient to produce said dialkybenzene isomer. The preferred molecular sieve catalysts have pores or surface cavities greater than 5.6 Angstroms in diameter and/or an X-ray diffraction pattern including d-spacing maxima at 12.4±0.25, 6.9±0.15, 3.57±0.07, and 3.42±0.07 Angstrom.

9 Claims, 1 Drawing Sheet

PRODUCTION OF DIALKYLBENZENES

RELATED APPLICATIONS

This application claims the benefit of Provisional Application No. 60/508,831, filed Oct. 3, 2003, the disclosure of which is incorporated by reference.

FIELD OF THE INVENTION

The present invention relates to a process for producing a desired dialkylbenzene isomer by transalkylation of undesired isomer(s) with a monoalkylbenzene compound over a molecular sieve catalyst.

BACKGROUND OF THE INVENTION

A variety of processes for production of specific alkylaromatic compounds are currently practiced in industry. Many such processes involve an alkylation step to produce the desired alkylaromatic compound and a separate transalkylation step to convert the undesired by-products back to reactants for recycle to the alkylation process. Processes for producing specific desired isomers of alkylaromatic compounds are generally more complex. Examples of desired isomers of alkylaromatic compounds are meta-diisopropylbenzene and para-diisopropylbenzene.

In typical processes for the production of diisopropylbenzenes (DIPBs), cumene is alkylated with propylene in the presence of an alkylation catalyst under reaction conditions suitable for the production of DIPBs. Typically, a particular facility does not have use for all of the products of the alkylation reaction, and the undesired byproducts are generally transalkylated with a benzene co-feed to produce cumene for recycle to the alkylation reactor. Meta- and para-DIPB are important intermediates in organic synthesis of resorcinol and hydroquinone, respectively.

DIPB can also be produced by separation from the polyalkylated by-product of the alkylation of benzene with propylene to produce cumene. However, DIPB separated from the polyalkylated fraction of current commercial cumene plants is rich in the kinetically preferred para- and ortho-DIPB isomers, making this route of limited use in the synthesis of meta-DIPB.

The term "transalkylation" is generally used to mean the exchange of alkyl substituent groups between aromatic hydrocarbons. The aromatic hydrocarbons can comprise a single alkyl substituted aromatic hydrocarbon or a mixture of aromatic hydrocarbons, provided that in the case of a mixture at least one of the components is an alkyl substituted aromatic hydrocarbon. A common transalkylation reaction is the reaction of a dialkylaromatic with benzene to produce a monoalkylaromatic product. Other examples of transalkylation reactions include disproportionation and isomerization.

U.S. Pat. No. 2,848,514 discloses a process for producing DIPBs including isomerization of ortho-, meta-, and optionally para-DIPB over a cracking catalyst to obtain a stream with less than 5% ortho- as a percentage of total DIPBs and also transalkylating polyisopropylbenzenes with benzene and/or cumene over a cracking catalyst to obtain a stream with less than 5% ortho- as a percentage of total DIPBs.

U.S. Pat. No. 3,763,259 discloses a process for producing DIPBs including disproportionating cumene with polyisopropylbenzenes and isomerization of the disproportionation product with ortho-and meta-DIPB. The disproportionation catalyst is a boron halide-modified inorganic oxide or a crystalline alumino-silicate.

GB Patent No. 755,956 discloses a process in which para-DIPB is prepared by isomerization of ortho- and meta-DIPB by heating with boron or aluminum halides and by transalkylation of higher alkylated products with benzene or cumene, also by heating with boron or aluminum halides.

GB Patent No. 786,305 discloses a process in which para-DIPB is prepared by isomerization of ortho- and meta-DIPB with an aluminum silicate catalyst comprising 85-90% $SiO_2$, 10-15% $Al_2O_3$, and 0.1-0.2% $H_2O$.

U.S. Pat. No. 4,375,575 discloses isomerization of DIPBs over a catalyst prepared by impregnating dehydrated amorphous silica gel with aluminum hydride.

NL Patent No. 85,204 discloses a process for transalkylating di-, tri-, or polyisopropylbenzenes with benzene and/or cumene over an aluminum silicate catalyst containing 0.1-0.2 wt. % water.

U.S. Pat. No. 4,822,943, which is herein fully incorporated by reference, discloses a process for the selective production of para-DIPB by reacting cumene and/or benzene with propylene over the molecular sieve ZSM-12.

U.S. Pat. No. 5,329,059, which is herein fully incorporated by reference, discloses a process for the disproportionation of an alkylaromatic compound, wherein the alkyl group has from 1 to about 6 carbon atoms, e.g., cumene, by contacting said compound with catalyst comprising an active form of synthetic porous crystalline MCM-49.

U.S. Pat. No. 6,049,018, which is herein fully incorporated by reference, discloses the porous crystalline material MCM-68 and its use in the alkylation of aromatics with short chain ($C_2$-$C_6$) olefins (for example, the alkylation of benzene with ethylene or propylene to produce ethylbenzene or cumene respectively), the transalkylation of aromatics (for example, the transalkylation of polyethylbenzenes or polyisopropylbenzenes with benzene to produce ethylbenzene or cumene respectively), and the disproportionation of alkylaromatics (for example, the disproportionation of toluene to produce xylenes).

In one process for production of p-DIPB, cumene is alkylated with propylene to produce mixed DIPBs, the para-DIPB is separated out, benzene is co-fed with meta- and ortho-DIPB to a reactor containing MCM-22 where transalkylation takes place, and the resulting cumene product is recycled to the alkylation reactor and re-alkylated with propylene to form mixed DIPBs. The para-DIPB is separated and the meta- and ortho-DIPB are recycled to the transalkylation reactor.

Although the feedstocks for alkylbenzene production generally include benzene, the handling of benzene is subject to numerous safety and environmental restrictions, making its use as a feedstock less desirable from a safety, environmental, and economic perspective.

SUMMARY OF THE INVENTION

This invention provides a process for producing a dialkylbenzene isomer having a formula $R_2C_6H_4$ wherein R is a given alkyl substituent, said process comprising contacting a polyalkylbenzene compound of formula $R_nC_6H_{6-n}$, where n is an integer between 2 and 4, with a monoalkylbenzene compound of formula $RC_6H_5$ in the presence of a molecular sieve catalyst under reaction conditions sufficient to produce said dialkylbenzene isomer.

In one embodiment, the dialkylbenzene isomer is a para-dialkylbenzene isomer, preferably para-diisopropylbenzene. In an other embodiment, the dialkylbenzene isomer is a meta-dialkylbenzene isomer, preferably meta-diisopropylbenzene.

The molecular sieve catalyst of the present invention preferably comprises a zeolite, preferably a zeolite with pores defined by at least 12 ring structures. Alternatively, the zeolite has pores and/or surface cavities with at least one cross-sectional dimension greater than 5.6 Angstroms. Some preferred zeolites are mordenite, ZSM-12, beta, MCM-68, zeolite X, zeolite Y, Ultrastable Y (USY), zeolite L, and zeolite omega.

One classification of suitable zeolites are those having an X-ray diffraction pattern including d-spacing maxima at 12.4±0.25, 6.9±0.15, 3.57±0.07, and 3.42±0.07 Angstrom. Some preferred zeolites having this x-ray diffraction pattern are ERB-1, ITQ-1, ITQ-2, MCM-22, MCM-36, MCM-49, MCM-56, PSH-3, or SSZ-25.

This invention can also be embodied in an integrated process for producing a desired dialkylbenzene isomer having a formula $R_2C_6H_4$, wherein R is a given alkyl substituent, with the following steps:

a) an alkylation step wherein a monoalkylbenzene compound having a formula $RC_6H_5$ is contacted with an alkylating agent in the presence of an alkylation catalyst and under alkylation conditions to produce a primary product comprising said desired dialkylbenzene isomer.

b) a separation step wherein the desired dialkylbenzene isomer is removed from the primary product to produce a first separated product stream; and c) a reaction step in which the first separated product stream is contacted with a monoalkylbenzene compound of formula $RC_6H_5$ in the presence of a molecular sieve catalyst under reaction conditions sufficient to produce a secondary product stream comprising said desired dialkylbenzene isomer.

Preferably the integrated process also has a separation step in which the desired dialkylbenzene isomer is removed from the secondary product stream to produce a second separated product stream which is blended with the first separated product stream prior to step (c).

DETAILED DESCRIPTION OF THE INVENTION

Introduction

Figure 1:
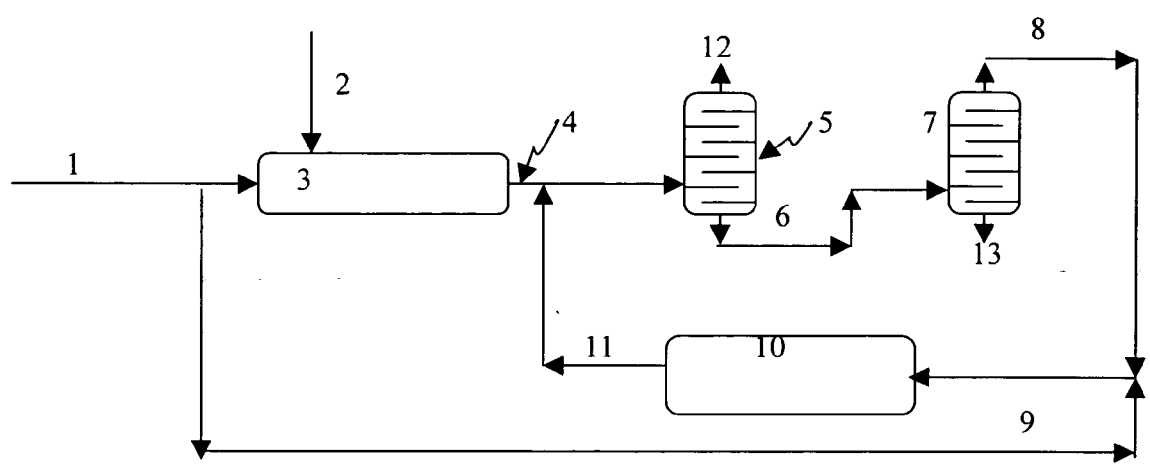
FIG. 1 shows a possible integrated process embodying the present invention.

This invention is directed toward a process for producing a dialkylbenzene isomer having a formula $R_2C_6H_4$, where R is a given alkyl substituent, and the process comprises contacting a polyalkylbenzene compound of formula $R_nC_6H_{6-n}$, where n is an integer between 2 and 4, with a monoalkylbenzene compound of formula $RC_6H_5$ in the presence of a molecular sieve catalyst under reaction conditions sufficient to produce said dialkybenzene isomer. It has been found that transalkylation using a monoalkylbenzene, as opposed to benzene, in the reaction results in increased production of the desired isomer in the transalkylation reaction, thereby reducing the recycle to the alkylation unit and increasing the total throughput capacity of an integrated process. Additionally, the safety and environmental risks and related mitigation costs can be reduced by elimination of a separate benzene feed to the process.

While the elimination of benzene as a feedstock is one of the benefits of the present invention, benzene is the desired aromatic nucleus of the compounds described herein. Compounds of a benzene structure which possess a hetero atom can also be useful provided they do not act as catalyst poisons under the reaction conditions selected.

Substituted benzene compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Generally the alkyl groups which can be present as substituents on the aromatic compound contain from 1 to about 22 carbon atoms, usually from about 1 to 8 carbon atoms, and most usually from about 1 to 4 carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, o-diisopropylbenzene, m-diisopropylbenzene, p-diisopropylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; and 4-ethyl-m-xylene.

Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene and pentadecyltoluene. Very often alkylate is obtained as a high boiling fraction in which the alkyl group attached to the aromatic nucleus varies in size from about $C_6$ to about $C_{12}$.

Reformate containing substantial quantities of benzene, toluene and/or xylene constitutes a useful feed for the alkylation process of this invention. A feedstock comprising substantially a single monoalkylbenzene compound would be preferred to minimize required separation steps in achieving a particular dialkylbenzene isomer.

The alkylating agents which are useful in the process of this invention generally include any aliphatic or aromatic organic compound having one or more available alkylating aliphatic groups capable of reaction with the alkylatable aromatic compound.

Preferably, the alkylating agent employed herein has at least one alkylating aliphatic group possessing from 1 to 5 carbon atoms. Examples of such alkylating agents are olefins such as ethylene, propylene, the butenes, and the pentenes; alcohols (inclusive of monoalcohols, dialcohols and trialcohols) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides.

Although mixtures of alkylating agents may be used, such as for example mixtures of light olefins, in the alkylation process of the present invention, it is preferred to use a single alkylating agent to minimize separation steps required.

Alternatively, the alkylating agent used in the process of the invention can have one or more alkylating aliphatic groups with at least about 6 carbon atoms, preferably at least about 8, and still more preferably at least about 12 carbon atoms. Examples of suitable long chain alkylating agents are olefins such as hexenes, heptenes, octenes, nonenes, decenes, undecenes, and dodecenes; alcohols (inclusive of monoalcohols, dialcohols, and trialcohols) such as hexanols, heptanols, octanols, nonanols, decanols, undecanols, and dodecanols; alkyl halides such as hexyl chlorides, octyl chlorides, dodecyl chlorides; and higher homologs of the foregoing. Branched alkylating agents, especially oligomerized olefins such as the trimers, tetramers, and pentamers of light olefins, such as ethylene, propylene, and butylenes, are also useful herein.

Monoalkylbenzene compounds useful in the present invention include, but are not limited to, ethylbenzene, cumene, toluene, and sec-butylbenzene.

In a preferred embodiment of this invention, alkylation and transalkylation are conducted in an integrated process with the undesired alkylation products passed to the transalkylation reactor for conversion either to the desired isomer or to reactants which can then be recycled to the alkylation unit.

The transalkylation process of the invention comprises passing the aromatic feedstock containing mono- and polyalkylbenzene compounds to a reaction zone containing a catalyst which comprises a molecular sieve, preferably a molecular sieve having pores and/or surface cavities with at least one cross-sectional dimension greater than 5.6 Angstroms.

In one embodiment, the molecular sieve used as the catalyst is a molecular sieve having pores which have at least one cross-sectional dimension greater than 5.6 Angstroms. Examples of suitable large pore molecular sieves include zeolite X, zeolite Y, dealuminized zeolite Y, Ultrastable Y (USY), ZSM-12, MCM-68, mordenite, zeolite beta, zeolite L, and zeolite omega. Dealuminized zeolite Y (Deal Y) may be prepared by the method found in U.S. Pat. No. 3,442,795. Low sodium Ultrastable Y (USY) is described in U.S. Pat. Nos. 3,293,192 and 3,449,070. ZSM-12 is described in U.S. Pat. No. 3,832,449. Zeolite beta is described in U.S. Pat. No. 3,308,069.

In an alternative embodiment, the molecular sieve used as the catalyst is a molecular sieve having surface cavities with at least one cross-sectional dimension greater than 5.6 Angstroms. In this case, the pores of the molecular sieve may have cross-sectional dimensions greater, less than, or equal to 5.6 Angstroms. Examples of molecular sieves having such surface cavities are ERB-1, ITQ-1 (described in U.S. Pat. No. 6,077,498), ITQ-2 (described in International Patent Publication Nos. WO97/17290 and WO01/21562), MCM-22 (described in U.S. Pat. No. 4,954,325), MCM-36 (described in U.S. Pat. No. 5,250,277), MCM-49 (described in U.S. Pat. No. 5,236,575), MCM-56 (described in U.S. Pat. No. 5,362,697), PSH-3 (described in U.S. Pat. No. 4,439,409), and SSZ-25 (described in U.S. Pat. No. 4,826,667). The entire contents of each of the aforementioned patents and applications are incorporated herein by reference.

In an alternative embodiment, the molecular sieve used as the catalyst is a molecular sieve having an X-ray diffraction pattern including d-spacing maxima at 12.4±0.25, 6.9±0.15, 3.57±0.07, and 3.42±0.07 Angstrom. Examples of molecular sieves having such an X-ray diffraction pattern are ERB-1, ITQ-1 (described in U.S. Pat. No. 6,077,498), ITQ-2 (described in International Patent Publication Nos. WO97/17290 (now U.S. Pat. No. 6,231,751) and WO01/21562), MCM-22 (described in U.S. Pat. No. 4,954,325), MCM-36 (described in U.S. Pat. No. 5,250,277), MCM-49 (described in U.S. Pat. No. 5,236,575), MCM-56 (described in U.S. Pat. No. 5,362,697), PSH-3 (described in U.S. Pat. No. 4,439,409), and SSZ-25 (described in U.S. Pat. No. 4,826,667).

The X-ray diffraction data used throughout this specification were obtained by standard techniques using the K-alpha doublet of copper as the incident radiation and a diffractometer equipped with a scintillation counter and associated computer as the collection system.

Zeolites are classified by the Structure Commission of the International Zeolite Association according to the rules of the IUPAC Commission on Zeolite Nomenclature. A framework-type describes the topology and connectivity of the tetrahedrally coordinated atoms constituting the framework and makes an abstraction of the specific properties for those materials. Molecular sieves for which a structure has been established are assigned a three letter code and are described in the *Atlas of Zeolite Framework Types,* 5th edition, Elsevier, London, England (2001), which is herein fully incorporated by reference.

Other molecular sieves include those described in R. Szostak, *Handbook of Molecular Sieves*, Van Nostrand Reinhold, New York, N.Y. (1992), which is herein fully incorporated by reference.

The molecular sieve used in the reaction zone of the process of the invention will typically be in the form of particles, for example extrudate, spheres or pellets, which contain the molecular sieve together with a binder system to improve physical integrity. The binder system can be any of a number of amorphous metal oxides including alumina, silica, zirconia, and titania, with alumina being preferred.

As in the case of many catalysts, it may be desirable to incorporate the molecular sieve used in the catalyst of the invention with another component resistant to the temperatures and other conditions employed in dialkylbenzene transalkylation reactions. Such components include active and inactive materials and synthetic or naturally occurring zeolites as well as inorganic materials such as clays, silica, and/or metal oxides such as alumina. The latter may be either naturally occurring or in the form of gelatinous precipitates or gels including mixtures of silica and metal oxides. Use of a component which is active tends to change the conversion and/or selectivity of the catalyst in the reaction process. Inactive components suitably serve as diluents to control the amount of conversion in the process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with molecular sieve include the montmorillonite and kaolin family, which families include the subbentonites, and the kaolins commonly known as Dixie, McNamee, Ga., and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the molecular sieve used herein also include inorganic oxides, such as silica, zirconia, titania, magnesia, beryllia, alumina, and mixtures thereof.

In addition to the foregoing materials, the molecular sieve can be composited with a porous matrix material such as silica-alumina, silica-magnesia, silica-zirconia, silica-thoria, silica-beryllia, and silica-titania as well as ternary compositions such as silica-alumina-thoria, silica-alumina-zirconia, silica-alumina-magnesia, and silica-magnesia-zirconia.

The relative proportions of molecular sieve and inorganic oxide matrix vary widely, with the molecular sieve content ranging from about 1 to about 90 percent by weight and more usually, particularly when the composite is prepared in the form of beads, in the range of about 2 to about 80 weight percent of the composite.

One embodiment of the present is a process for producing a dialkylbenzene isomer having a formula $R_2C_6H_4$, wherein R is a given alkyl substituent, by combining undesired isomers of the same dialkylbenzene with a monoalkylbenzene having the same substituent alkyl group R in the presence of a molecular sieve catalyst under reaction conditions sufficient to produce an effluent containing the desired dialkylbenzene isomer. Optionally, trialkylbenzenes and heavier polyalkylbenzenes may also be fed to the transalkylation reaction. Preferably, the effluent is subjected to a series of separation steps in which benzene, monoalkylbenzene, undesired dialkylbenzene isomer(s), trialkylbenzenes, polyalkylbenzenes, and heavies are separated from the desired dialkylbenzene isomer(s), and optionally from each other. Preferably, the monoalkylbenzene and the undesired dialkylbenzene(s) are recycled to the transalkylation reactor, optionally with benzene and other components from the effluent which were not separated from the monoalkylaromatic. Optionally the trialkylbenzenes are also recycled to the transalkylation reactor. Polyalkylbenzenes may also optionally be recycled to the transalkylation reactor, preferably in relatively small quantities, more preferably less than 5 wt. %.

Preferably, the transalkylation reaction of the above embodiment is part of an integrated process along with at least one dialkylbenzene production step, such that the feed to the transalkylation reactor comprises part of the effluent from the dialkylbenzene production step, preferably after separation of at least the desired dialkylbenzene isomer(s) from that effluent. Preferably the dialkylbenzene production step of the integrated process is an alkylation reaction, more preferably an alkylation reaction in which a monoalkylbenzene is alkylated by an alkylating agent having the same alkyl substituent as the monoalkylbenzene.

FIG. 1 shows one possible embodiment of the present invention where a monoalkylbenzene stream (1) comprising a monoalkylbenzene compound of formula $RC_6H_5$, where R is an alkyl group, and an alkylating agent (2) also comprising an alkyl group R are fed to an alkylation reactor (3) which contains an alkylation catalyst and operates at alkylation conditions. The primary product stream (4) comprises a mixture of dialkylbenzene isomers having the formula $R_2C_6H_4$. That primary product stream (4) is introduced to a separation step (5) wherein the desired dialkylbenzene isomer (12) is removed from the primary product to produce a first depleted product stream (6). Optionally, lighter components of the effluent are removed in one or more separation step(s) preceding removal of the desired dialkylbenzene isomer. The first depleted product stream (6) is sent to another one or more separation step(s) (7) in which heavier components (13), optionally including trialkylbenzenes and heavier polyalkylbenzenes, are removed to provide a first separated product stream (8). The first separated product stream (8) is contacted with a monoalkylbenzene compound (9) of formula $RC_6H_5$ in a reactor (10) in the presence of a molecular sieve catalyst under reaction conditions sufficient to produce a secondary product stream (11) comprising said desired dialkylbenzene isomer. The secondary product stream (11) may then be blended with the primary product, stream (4) and subjected to separation steps (5) and (7) in which the desired dialkylbenzene isomer (12) is removed.

The conditions used in any of the above embodiments of the process of the invention should be such as to effect significant transalkylation of the dialkylbenzene(s) in the feed while minimizing the production of undesired by-products, such as trialkylbenzenes and other heavy materials. Suitable conditions include a WHSV in terms of total throughput in the transalkylation reactor in the range of 0.1 to 100 $hr^{-1}$, more preferably between about 1 and about 10 $hr^{-1}$. Preferably the temperature of the transalkylation reaction is between about 200 and about 600° F. (about 95 to about 315° C.), more preferably between about 300 and about 500° F. (about 150 to about 260° C.). The pressure is preferably in the range of about 300 to about 15000 kPa, more preferably about 1000 to about 4000 kPa and is sufficient to maintain the reactants in the liquid phase.

In one embodiment in which the desired dialkylbenzene isomer is para-DIPB, the feed to the transalkylation process is substantially comprised of cumene, meta-DIPB, and ortho-DIPB. Optionally, TIPB and higher poly-isopropylbenzenes may be included in the feed. Benzene produced in the alkylation (or disproportionation) and transalkylation reactions may be left in the feed to the transalkylation process. Preferably, TIPBs, and optionally higher poly-isopropylbenzenes, will be included in the feed to the transalkylation process if benzene comprises greater than about 2 wt. % of the feed to the transalkylation reaction, even more preferably if the benzene is greater than about 5 wt. %.

In another embodiment in which the desired dialkylbenzene isomer is meta-DIPB, the feed to the transalkylation process is substantially comprised of cumene and para-DIPB. Although para-DIPB can be separated from a mixture of DIPB isomers by super fractionation, the boiling points of ortho- and meta-DIPB are too close to allow effective separation of meta-DIPB by fractionation. Therefore, a desirable process for producing meta-DIPB would minimize the production of the ortho-isomer, preferably in both an initial DIPB production step and in a transalkylation step.

Currently, meta-DIPB is manufactured commercially by alkylating cumene with propylene over a homogeneous $AlCl_3$ catalyst. The high activity of the $AlCl_3$ catalyst produces a mixture of DIPB isomers with near equilibrium ortho content. This is advantageous since at equilibrium in the liquid phase between 50 and 150° C. the ratio of meta:ortho DIPB is greater than 100 providing sufficient purity for efficient downstream conversion to resorcinol. Process operation between 50 and 150° C. also results in DIPB products containing less than 1000 ppm of co-boiling n-propylisopropylbenzene impurities. However, corrosion and the need to neutralize, separate and recycle the $AlCl_3$ catalyst, make it difficult to employ.

U.S. Published Application No. US 2003-0028061 (A1) discloses a process for the disproportionation of cumene with a molecular sieve catalyst, preferably TEA-mordenite. The contacting step disproportionates at least part of the cumene in the feed to provide a disproportionation effluent containing benzene and a mixture of diisopropylbenzene isomers. The effluent contains less than 1% of ortho-diisopropylbenzene by weight of the total diisopropylbenzene content of said effluent, less than 1 wt. % of n-propylbenzene, less than 5 wt. % of triisopropylbenzenes and less than 5 wt. % of disproportionation products other than benzene and diisopropylbenzenes.

Co-pending U.S. application Ser. No. 10/299,558 (now U.S. Pat. No. 6,753,453) fully incorporated herein by reference, discloses a process for the selective production of meta-diisopropylbenzene by contacting cumene under disproportionation conditions and in the absence of added benzene with a catalyst comprising a porous crystalline inorganic oxide material having an X-ray diffraction pattern including d-spacing maxima at 12.4±0.25, 6.9±0.15, 3.57±0.07 and 3.42±0.07 Angstrom to produce a disproportionation effluent containing benzene and a mixture of diisopropylbenzene isomers, and then recovering from said disproportionation effluent a meta-diisopropylbenzene boiling range fraction in which the ratio of meta-diisopropylbenzene to ortho-diisopropylbenzene is in excess of 50 and the total amount of meta-diisopropylbenzene co-boilers excluding ortho-diisopropylbenzene is less than 1 wt. % of said fraction.

Optionally, TIPB and higher poly-isopropylbenzenes may be included in the feed to the transalkylation reactor. Benzene produced in the alkylation (or disproportionation) and transalkylation reactions may be left in the feed to the transalkylation process. Preferably, TIPBs, and optionally higher poly-isopropylbenzenes, will be included in the feed to the transalkylation process if benzene comprises greater than about 2 wt. % of the feed to the transalkylation reaction, even more preferably if the benzene is greater than about 5 wt. %.

While there is no benzene co-feed in the presently described process, it will be recognized by those of ordinary skill in the art that benzene is a natural byproduct of the reactions occurring in both the alkylation and transalkylation processes and can not be completely eliminated from the system. One benefit of the inventive process is the elimination of benzene handling and the resultant environmental and safety risks associated with transport to the DIPB process, particularly for plants which import benzene from other facilities.

Another alternative for eliminating a benzene feed from the integrated reaction process is isomerization of the undesired dialkylbenzenes without any co-feed. The catalysts and operating conditions described above would also be suitable for an isomerization reaction. Benefits of such a process include higher production of the desired dialkylbenzene product in the isomerization (transalkylation) reaction, which would then free up capacity for increased throughput in the alkylation unit. In this embodiment, it would be preferable to minimize trialkylbenzene and heavier feeds to the isomerization reactor.

EXAMPLES

In order to provide a better understanding of the present invention including representative advantages thereof, the following examples are offered. Example 1 (Comparative) will describe the results from a typical transalkylation reaction using benzene and primarily meta-DIPB as feeds in a 2:1 ratio. Examples 2 through 5 will demonstrate the performance of transalkylation using cumene instead of benzene in a 2:1 ratio at varying reaction temperatures, and Examples 6 and 7 will demonstrate the performance of the same reaction with higher WHSV. Examples 8 and 9 demonstrate the impact of using cumene in a 1:1 ratio with DIPB. Examples 10 through 12 demonstrate an alternative isomerization process in which dialkylbenzenes are fed to the reactor with no co-feed.

All experiments were conducted in a fixed-bed, ⅜" or ¾" OD tubular reactor in a downflow configuration. The reactor furnace was controlled in isothermal mode. Examples 1 through 12 were conducted using a commercially available MCM-22 catalyst. The catalyst was dried off-line at 260° C. in air for two hours before loading. Experiments were conducted with ¹⁄₁₆" cylindrical extrudates and used two grams (2 g) of catalyst as whole extrudates loaded into the ⅜" reactor. The catalyst bed was axially centered in the middle furnace zone. The catalyst was used as received without further sizing, but was packed with sand to fill the interstitial spaces.

Before introducing feed, the reactor was brought to the desired temperature and pressure under flowing nitrogen. After feed introduction, the reaction was monitored with an on-line gas chromatograph/flame ionization detector instrument. All experiments over the MCM-22 catalyst showed stable activity with no sign on deactivation over the time periods investigated (1-3 weeks).

The DIPB used in these studies was obtained from a commercial unit. Benzene (99.9±%) and Cumene (99%) were obtained from Aldrich. All feed blending components were used without further off-line pretreatment but feed blends were passed through molecular sieve in an on-line filter before contacting the catalyst bed. Gas chromatograph analyses of each of the feed compositions are provided in the example details below.

Effluent data for Examples 1 through 12 are shown in Table 1.

Example 1

Comparative

Example 1 shows the results of a base case with the traditional transalkylator feed in a 2:1 weight ratio of benzene to DIPB. The feed composition was 65.9 wt. % benzene, 30.9 wt. % meta-DIPB, 1.8 wt. % ortho-DIPB, and 0.4 wt. % para-DIPB. The reaction was conducted at a WHSV of 1 with a feed rate of 2 grams per hour and a temperature of 405° F. (207° C.). The effluent composition is shown in Table 1. It can be seen that the effluent was primarily benzene and cumene with 3.3 wt. % para-DIPB.

Examples 2 Through 5

Examples 2 through 5 were conducted using a 2:1 weight ratio of cumene to DIPB. The feed composition was 63.7 wt. % cumene, 32.6 wt. % meta-DIPB, 1.9 wt. % ortho-DIPB, and 0.4 wt. % para-DIPB. The reaction was conducted at a WHSV of 1 with a feed rate of 2 grams per hour and temperatures of 405° F. (207° C.), 355° F. (179° C.), 325° F. (163° C.), and 305° F. (152° C.), respectively. The effluent compositions are shown in Table 1. It can be seen that the effluent contained 4.1 to 15.5 wt. % para-DIPB. Decreasing temperature tended to reduce m-DIPB conversion and TIPB formation.

Examples 6 and 7

Examples 6 and 7 were conducted using a 2:1 weight ratio of cumene to DIPB. The feed composition was 63.7 wt. % cumene, 32.6 wt. % meta-DIPB, 1.9 wt. % ortho-DIPB, and 0.4 wt. % para-DIPB. The reaction was conducted at a WHSV of 2 with a feed rate of 4 grams per hour and temperatures of 355° F. (179° C.) and 340° F. (171° C.), respectively. The effluent compositions are shown in Table 1. It can be seen that the effluents contained 13.9 and 10.7 wt. % para-DIPB respectively.

Example 8

Example 8 was conducted using a 1:1 weight ratio of cumene to DIPB. The feed composition was 50.9 wt. % cumene, 44.2 wt. % meta-DIPB, 2.5 wt. % ortho-DIPB, and 0.6 wt. % para-DIPB. The reaction was conducted at a WHSV of 2 with a feed rate of 4 grams per hour and a temperature of 340° F. (171° C.). The effluent composition is shown in Table 1.

Example 9

Example 9 was conducted using a 1:1 weight ratio of cumene to DIPB. The feed composition was 50.9 wt. % cumene, 44.2 wt. % meta-DIPB, 2.5 wt. % ortho-DIPB, and 0.6 wt. % para-DIPB. The reaction was conducted at a WHSV of 1 with a feed rate of 2 grams per hour and a temperatures of 340° F. (171° C.). The effluent composition is shown in Table 1.

m-DIPB converted (decrease from 48 to 38 to 29% with increase of WHSV from 1 to 2 to 4). Although TIPB formation is much higher than in the base case, other experimental results suggest TIPB formation can be reduced further by decreasing temperature.

Example 13

Example 10 was repeated using a commercially available ZSM-12 catalyst prepared in the same manner as the MCM-22. Again, the feed was DIPB-only with the composition being 89.7 wt. % meta-DIPB, 5.1 wt. % ortho-DIPB, and 1.1 wt. % para-DIPB. The reaction was conducted at a WHSV of 1 with a feed rate of 2 grams per hour. The temperature was held constant at 405° F. (207° C.). The effluent composition at 4.5 days is shown in Table 1. It was noted that the ZSM-12 in the isomerization reaction showed signs of aging during the testing, whereas the MCM-22 did not show any signs of aging within one to three weeks of testing at different conditions.

TABLE 1

Effluent Compositions

| Ex. | Feed | WHSV | Temp (F.) | Benzene | Cumene | m-DIPB | o-DIPB | p-DIPB | C10, C11 others | TIPBs |
|---|---|---|---|---|---|---|---|---|---|---|
| 1 | 2:1 Benzene:DIPB | 1 | 405 | 0.500 | 0.370 | 0.071 | 0.001 | 0.033 | 0.015 | 0.007 |
| 2 | 2:1 Cumene:DIPB | 1 | 405 | 0.084 | 0.415 | 0.269 | 0.003 | 0.142 | 0.029 | 0.046 |
| 3 | 2:1 Cumene:DIPB | 1 | 355 | 0.061 | 0.460 | 0.280 | 0.003 | 0.155 | 0.008 | 0.027 |
| 4 | 2:1 Cumene:DIPB | 1 | 325 | 0.025 | 0.564 | 0.291 | 0.011 | 0.089 | 0.006 | 0.010 |
| 5 | 2:1 Cumene:DIPB | 1 | 305 | 0.012 | 0.594 | 0.321 | 0.016 | 0.041 | 0.006 | 0.006 |
| 6 | 2:1 Cumene:DIPB | 2 | 355 | 0.039 | 0.498 | 0.285 | 0.005 | 0.139 | 0.007 | 0.012 |
| 7 | 2:1 Cumene:DIPB | 2 | 340 | 0.027 | 0.540 | 0.291 | 0.009 | 0.107 | 0.007 | 0.012 |
| 8 | 1:1 Cumene:DIPB | 2 | 340 | 0.019 | 0.452 | 0.377 | 0.013 | 0.111 | 0.008 | 0.012 |
| 9 | 1:1 Cumene:DIPB | 1 | 340 | 0.031 | 0.433 | 0.341 | 0.006 | 0.154 | 0.008 | 0.020 |
| 10 | DIPB | 1 | 405 | 0.008 | 0.170 | 0.429 | 0.002 | 0.230 | 0.018 | 0.143 |
| 11 | DIPB | 2 | 405 | 0.006 | 0.116 | 0.477 | 0.000 | 0.257 | 0.018 | 0.117 |
| 12 | DIPB | 4 | 405 | 0.005 | 0.081 | 0.532 | 0.000 | 0.267 | 0.027 | 0.081 |
| 13 | DIPB | 1 | 405 | 0.0002 | 0.0245 | 0.6131 | 0.0451 | 0.2567 | 0.0231 | 0.0077 |

Reducing the amount of cumene in the feed relative to Examples 2 through 7, increased DIPB conversion while TIPB production remained approximately constant. Comparing Examples 8 and 9, m-DIPB converted increased from 0.14 to 0.26 g/hr when the cumene to DIPB feed ratio was reduced from 2:1 to 1:1.

Examples 10 Through 12

Examples 10 through 12 show the results of a DIPB-only feed to the same MCM-22 catalyst. These examples represent an alternative embodiment of the goal of removing feed benzene from the system. The feed composition was 89.7 wt. % meta-DIPB, 5.1 wt. % ortho-DIPB, and 1.1 wt. % para-DIPB. The reaction was conducted at WHSVs of 1, 2, and 4, respectively, with corresponding feed rates of 2, 4, and 8 grams per hour, respectively. The temperature was held constant at 405° F. (207° C.). The effluent compositions are shown in Table 1.

At equivalent temperature and WHSV, the DIPB feed results in a higher rate of m-DIPB conversion. At equivalent WHSV, m-DIPB is converted at twice the rate of the base case shown in Example 1. TIPB production is higher relative to Example 1. The formation of TIPB relative to m-DIPB converted can be reduced by operating the reactor at higher WHSV. Examples 11 and 12 demonstrate the effect of increasing WHSV to reduce TIBP production relative to

We claim:

1. A process for producing a product containing diisopropylbenzene isomer, said diisopropylbenzene isomer comprises para-diisopropylbenzene, said process comprising reacting a feed comprising polyisopropylbenzene compound of formula $R_nC_6H_{6-n}$, where n is an integer between 2 and 4 and wherein R is an isopropyl substituent, with cumene in the presence of a molecular sieve catalyst comprising MCM-22 zeolite under transalkylation reaction conditions sufficient to produce said product having higher para-diisopropylbenzene content than the para-diisopropylbenzene content in the feed.

2. The process of claim 1 wherein the diisopropylbenzene isomer further comprises a meta-diisopropylbenzene.

3. The process of claim 1 wherein the molecular sieve catalyst further comprises another zeolite, wherein the zeolite comprises pores defined by at least a 12 ring structure.

4. The process of claim 3 wherein the another zeolite has pores and/or surface cavities with at least one cross-sectional dimension greater than 5.6 Angstroms.

5. The process of claim 3 wherein the another zeolite is selected from the group consisting of mordenite, ZSM-12, beta, MCM-68, zeolite X, zeolite Y, Ultrastable Y (USY), zeolite L, or zeolite omega.

6. The process of claim 3 wherein the another zeolite has an X-ray diffraction pattern including d-spacing maxima at 12.4±0.25, 6.9±0.15, 3.57±0.07, and 3.42±0.07 Angstrom.

7. The process of claim 6 wherein the another zeolite is selected from the group consisting of ERB-1, ITQ-1, ITQ-2, MCM-36, MCM-49, MCM-56, PSH-3, and SSZ-25.

8. A process for producing a desired diisopropylbenzene isomer, said process comprising (a) An alkylation step wherein cumene is contacted with propylene in the presence of an alkylation catalyst and under alkylation conditions to produce a primary product comprising said desired diisopropylbenzene isomer and undesired polyisopropylbenzenes;

(b) a separation step wherein the desired diisopropylbenzene isomer is removed from the primary product to produce a first separated product stream containing undesired polyisopropylbenzenes; and (c) a reaction step in which the first separated product stream containing said undesired polyisopropylbenzenes is reacted with cumene in the presence of a molecular sieve catalyst comprising MCM-22 zeolite under transalkylation reaction conditions sufficient to produce a secondary product stream having higher para-diisopropylbenzene content than the para-diisopropylbenzene content in the first separated product stream.

9. The process of claim 8 wherein the desired diisopropylbenzene isomer is removed from the secondary product stream to produce a second separated product stream which is blended with the first separated product stream prior to step (c).

* * * * *